United States Patent [19]

Park et al.

[11] Patent Number: 5,336,434
[45] Date of Patent: Aug. 9, 1994

[54] METHODS, COMPOSITIONS AND APPARATUS TO DISINFECT LENSES

[75] Inventors: John Y. Park, Santa Ana; Paul S. Ripley, Irvine, both of Calif.; Anthony J. Dziabo, Lake Forest, all of Calif.

[73] Assignee: Allergan, Inc., Irvine, Calif.

[21] Appl. No.: 974,399

[22] Filed: Nov. 10, 1992

Related U.S. Application Data

[63] Continuation-in-part of Ser. No. 906,817, Jun. 30, 1992, which is a continuation-in-part of Ser. No. 664,601, Mar. 4, 1991, which is a continuation-in-part of Ser. No. 416,074, Oct. 2, 1989, Pat. No. 5,078,908, and Ser. No. 461,405, Jan. 5, 1990, Pat. No. 5,279,673, and Ser. No. 461,540, Jan. 5, 1990, Pat. No. 4,997,626.

[51] Int. Cl.⁵ ............................................. C09K 3/00
[52] U.S. Cl. ................................. 252/187.21; 424/661; 435/264
[58] Field of Search .............. 252/187.21; 424/663, 424/661; 435/264

[56] References Cited

U.S. PATENT DOCUMENTS

| Re. 23,218 | 4/1950 | Levy | 162/87 |
|---|---|---|---|
| Re. 32,672 | 5/1988 | Huth et al. | 252/95 |
| 2,436,134 | 2/1948 | Aston | 423/477 |
| 3,123,521 | 3/1964 | Wentworth | 424/615 |
| 3,278,447 | 10/1966 | McNicholas | 252/186.21 |
| 3,591,515 | 7/1971 | Lovely | 252/186.22 |
| 3,819,828 | 6/1974 | McCoy | 424/71 |
| 3,910,296 | 10/1975 | Karageozian et al. | 134/42 |
| 3,912,451 | 10/1975 | Gaglia, Jr. | 422/30 |
| 4,011,941 | 3/1977 | Parsons | 206/5.1 |
| 4,084,747 | 3/1978 | Alliger | 422/20 |
| 4,104,190 | 8/1978 | Hartshorn | 252/187.21 |
| 4,123,376 | 10/1978 | Gray | 252/99 |
| 4,146,496 | 3/1979 | Gray | 252/99 |
| 4,386,160 | 5/1983 | Branner-Jorgensen | 435/221 |
| 4,456,510 | 6/1984 | Murakami | 201/101 |
| 4,459,217 | 7/1984 | Bogie | 252/174.14 |
| 4,499,077 | 2/1985 | Stockel et al. | 424/661 |
| 4,557,925 | 12/1985 | Lindahl et al. | 424/482 |
| 4,568,517 | 2/1986 | Kaspar et al. | 422/30 |
| 4,614,549 | 9/1986 | Ogunbuyi et al. | 122/330 |
| 4,618,444 | 10/1986 | Hudson et al. | 252/92 |

(List continued on next page.)

FOREIGN PATENT DOCUMENTS

| 520668 | 12/1987 | Australia. |
|---|---|---|
| 0082798 | 6/1983 | European Pat. Off. . |
| 0147100 | 7/1985 | European Pat. Off. . |
| 0168253 | 1/1986 | European Pat. Off. . |
| 0196075 | 1/1986 | European Pat. Off. . |
| 0199385 | 10/1986 | European Pat. Off. . |

(List continued on next page.)

OTHER PUBLICATIONS

Chemical Abstracts Selects: Issue Feb. 1987.
Eudragit L Data Sheet (Info L-2/e).
Siu et al, "Effect of Succinylation on the Protein Quality and Urinary Excretion of Bound and Free Amino Acids", J. Agric. Food Chem. 1982, 30, 1179–1183.
Communications to the Editor, "Stabilization of Microbial Proteases against Autolysis Using Acylation with Dicarboxylic Acid Anhydrides", Biotechnology and Bioengineering, vol. XXIV, pp. 483–486 (1982).
Kennedy et al, "The Oxidation of Organic Substances

(List continued on next page.)

Primary Examiner—Richard D. Lovering
Assistant Examiner—Valerie Fee
Attorney, Agent, or Firm—Frank J. Uxa

[57] ABSTRACT

Methods for disinfecting a lens are disclosed. In one embodiment, the methods comprise contacting a lens, e.g., a contact lens, to be disinfected with a liquid medium containing stabilized chlorine dioxide and an activator component selected from chlorine dioxide reducing agents and mixtures thereof to effect formation of chlorine dioxide from the stabilized chlorine dioxide, thereby disinfecting the lens. Compositions and apparatus useful in the above-noted methods are also disclosed.

17 Claims, 1 Drawing Sheet

U.S. PATENT DOCUMENTS

| | | | |
|---|---|---|---|
| 4,654,208 | 3/1987 | Stockel et al. | 424/78.08 |
| 4,689,215 | 8/1987 | Ratcliff | 424/53 |
| 4,690,773 | 9/1987 | Ogunbuyi et al. | 252/174.12 |
| 4,767,559 | 8/1988 | Kruse et al. | 252/106 |
| 4,792,442 | 12/1988 | Ratcliff | 408/54 |
| 4,861,514 | 8/1989 | Hutchings | 252/187.21 |
| 4,885,135 | 8/1989 | Ratcliff | 424/661 |
| 4,986,990 | 1/1991 | Davidson et al. | 424/665 |
| 4,997,626 | 3/1991 | Dziabo et al. | |
| 5,077,258 | 12/1991 | Phillips | 502/321 |
| 5,078,908 | 1/1992 | Ripley et al. | |
| 5,129,999 | 7/1992 | Holland et al. | |
| 5,135,623 | 8/1992 | Dziabo et al. | 204/101 |
| 5,159,912 | 10/1992 | Dziabo et al. | 252/106 |

FOREIGN PATENT DOCUMENTS

| | | |
|---|---|---|
| 0209071 | 1/1987 | European Pat. Off. |
| 0240315 | 10/1987 | European Pat. Off. |
| 0279401 | 2/1988 | European Pat. Off. |
| 0255041A1 | 5/1988 | European Pat. Off. |
| 0278224 | 8/1988 | European Pat. Off. |
| 0458578A2 | 11/1991 | European Pat. Off. |
| 3626082A1 | 11/1988 | Fed. Rep. of Germany |
| WO8504107 | 9/1985 | PCT Int'l Appl. |
| WO8605695 | 10/1986 | PCT Int'l Appl. |
| WO9109632 | 7/1991 | PCT Int'l Appl. |
| 9109690 | 7/1991 | PCT Int'l Appl. |
| WO9215334 | 9/1991 | PCT Int'l Appl. |
| 1269677 | 4/1982 | United Kingdom |
| 2139260 | 11/1984 | United Kingdom |
| 2173017A | 10/1986 | United Kingdom |
| 2187748A | 9/1987 | United Kingdom |
| 2187748 | 9/1987 | United Kingdom |
| 2151039A | 7/1988 | United Kingdom |

OTHER PUBLICATIONS by Potassium Peroxymonosulfate", J. Organic Chemistry 25:1901–1906 (1960).

Polymers Letters Edition, "A Study of Ozone Attack on Elastomer Surfaces By Attenuated Total Reflectance Spectroscopy", vol. 12, pp. 281–286.

Manivannan et al, "Peroxo Salts As Initiators Of Vinyl Polymerization-II" Eur. Polym. J. vol. 23, No. 4, pp. 311–313 (1987).

Evans et al, "Phase Transfer Controlled Selective Oxidation Of Diarylsulfides to Diarylsulfoxides Using Potassium Hydrogen Persulfate", Synthetic Communications, 16(10), 1207–1216 (1986).

Bloch et al, "Epoxidation of Alkenes with Potassium Hydrogen Persulfate", J. Org. Chem. 1985, 50, 1544–1545.

Ball, Jr. et al., "Acylation of Egg White Proteins with Acetic Anhydride and Succinic Anhydride", Poultry Science 1982 61:1041–1046.

W. Masschelein, "Preparation of Pure Chlorine Dioxide", vol. 6, No. 2, Jun. 1967.

I. Klotz, "Succinylation", Methods in Enzymology, vol. XI, Enzyme Structure, 1967, 576–580.

De Poorter et al, "Ozone As Oxygen Donor In The Catalytic Hydroxylation of Saturated Hydrocarbons", Tetrahedron Letters, vol. 26, No. 37, pp. 4459–4462 (1985).

Trost et al, "Chemoselective Oxidation of Sulfides to Sulfones with Potassium Hydrogen Persulfate", Tetrahedron Letters, vol. 22, No. 14, pp. 1287–1290 (1981).

METHODS, COMPOSITIONS AND APPARATUS TO DISINFECT LENSES

RELATED APPLICATIONS

This application is a continuation-in-part of copending application Ser. No. 906,817, filed Jun. 30, 1992, now pending which in turn, is a continuation-in-part of application Ser. No. 664,601, filed Mar. 4, 1991 now pending which, in turn, is a continuation-in-part of each of the following applications: Ser. No. 416,074 filed Oct. 2, 1989 now U.S. Pat. No. 5,078,908; Ser. No. 461,405 filed Jan. 5, 1990 now U.S. Pat. No. 5,279,673; and Ser. No. 461,540 filed Jan. 5, 1990 now U.S. Pat. No. 4,997,626. Each of these applications is incorporated in its entirety by reference herein.

BACKGROUND OF THE INVENTION

This invention relates to disinfecting lenses, such as contact lenses. In particular, the invention relates to methods, compositions and apparatus useful to quickly and effectively disinfect lenses while reducing eye irritation caused by disinfecting the lenses.

Contact lenses should be periodically disinfected to protect the wearer's eyes from infection and to improve the wearer's comfort. It is often desirable that lens disinfecting be accomplished quickly, e.g., for the convenience of the wearer. However, conventional fast-acting disinfectants that are used with contact lenses have a high potential to cause eye irritation. In fact, the general rule has been that the amount of eye irritation to be expected is directly proportional to the rate of disinfecting. Fast-acting disinfectants, such as hydrogen peroxide, cause significant ocular irritation if placed directly in the eye. Thus, when using such disinfectants a thorough rinsing and/or neutralization step is required to remove substantially all traces of the disinfectant. Thus, in Gaglia, et al U.S. Pat. No. 3,912,451 a metal component is used to remove hydrogen peroxide from soft contact lenses which have been sterilized with hydrogen peroxide. Also, such disinfectants are often not stable and tend to lose their potency over time.

It has been proposed to disinfect substrates using an acidic solution containing chlorites, such as sodium chlorite. Alliger U.S. Pat. No. 4,084,747 and International Patent Publication (PCT) No. WO35/04107 are directed to such systems. The acidic conditions apparently cause liberation of chlorine dioxide, which acts as a disinfectant. High acidity can cause substantial eye irritation. This potential eye irritation risk can be reduced or eliminated by avoiding acidic conditions in treating contact lenses.

European Patent Publication 0196075 discloses a contact lens cleaning system of an aqueous chlorite solution and a solid component containing an agent for accelerating decomposition of chlorite, such as an acid or a reducing agent, to form free oxygen, and an oxygen consumption agent, such as a sugar. This publication discloses that the chlorite decomposes to form free oxygen which removes impurities from a lens to be cleaned. The oxygen consumption agent is disclosed as preventing excess free oxygen from attacking the lens after the impurities have been removed. This publication does not disclose or suggest any contact lens disinfecting, or the use of stabilized chlorine dioxide.

In addition to disinfecting the contact lens, it should also be cleaned, for example, of debris such as protein-based debris which accumulates on the lens during use. Such lens cleaning is often done in the presence of one or more enzymes. See, for example, Karageozian U.S. Pat. No. 3,910,296. In many instances, a complete lens maintenance procedure involves first enzymatic cleaning followed by the separate lens disinfecting step. One system in which lens cleaning and disinfecting occur substantially simultaneously is disclosed in Huth, et al U.S. Pat. Re. No. 32,672. This system employs a solution to contact the lens which comprises a disinfecting amount of peroxide and an effective amount of peroxide-active proteolytic enzyme for a time sufficient to remove substantially all protein accretions and to disinfect the lens.

SUMMARY OF THE INVENTION

New methods, compositions and apparatus for disinfecting lenses, for example, contact lenses, have been discovered. The present system utilizes the controlled formation of chlorine dioxide, a very effective contact lens disinfectant. The ability to control the formation of chlorine dioxide allows one to effectively and efficiently ship and store the chlorine dioxide precursor prior to use. Then, substantially on demand, the precursor is activated to provide the desired amount of chlorine dioxide. In addition, the present system preferably provides for maintaining the acidity of the medium in which the lens is present within the physiological range, for example, in the range of about 6 to about 10, so that no acidity adjustment is needed after disinfection. This feature of the present invention substantially reduces the risk of eye irritation caused by the disinfecting procedure.

In one broad aspect, the invention involves methods for disinfecting a lens. In one embodiment, a lens to be disinfected is contacted with a composition including a liquid medium and a chlorine dioxide precursor, preferably stabilized chlorine dioxide. This contacting takes place in the presence of an effective amount of an activator component selected from chlorine dioxide reducing components and mixtures thereof in an amount to effect formation of a lens disinfecting amount of chlorine dioxide from the chlorine dioxide precursor in the liquid medium. This contacting results in the lens being disinfected. This contacting preferably occurs so that the pH of the liquid medium is within the physiological range for humans, for example, within the range of about 6 to about 10, more preferably within the range of about 6 to about 8. Maintaining such a pH allows a contact lens disinfected in accordance with the present invention to be placed directly into the wearer's eye. Alternately, a simple saline rinse or soak of the disinfected contact lens may be employed before placing the lens back in the wearer's eye.

In another broad aspect of the invention, compositions, which are useful in performing the present methods, are provided. In one embodiment, the present compositions comprise a liquid medium containing stabilized chlorine dioxide, preferably in an amount more than that effective, when activated, to form a contact lens disinfecting amount of chlorine dioxide; and an activator component selected from chlorine dioxide reducing components and mixtures thereof in an amount effective when released in the liquid medium to effect formation of a contact lens disinfecting amount of chlorine dioxide from the stabilized chlorine dioxide in the liquid medium.

In another embodiment, compositions useful for disinfecting contact lenses are provided which comprise a solid chlorine dioxide precursor in an amount more than that effective, when activated, to form a contact lens disinfecting amount of chlorine dioxide; and a solid activator component selected from chlorine dioxide reducing components and mixtures thereof. This solid activator component is present in an amount effective, when released in a liquid medium containing a soluble chlorine dioxide precursor derived from the solid chlorine dioxide precursor, to effect the formation of a contact lens disinfecting amount of chlorine dioxide from the soluble chlorine dioxide precursor.

In another broad aspect of the present invention, apparatus useful for dispensing contact lens disinfectants are provided. In one embodiment, such apparatus comprise a first container section defining a first reservoir sized and adapted for holding a first liquid medium containing a chlorine dioxide precursor, for example, stabilized chlorine dioxide. A second container section is provided which defines a second reservoir sized and adapted for holding a second liquid medium containing an activator component, for example, selected from chlorine dioxide reducing components and mixtures thereof. This activator component is effective, when combined with the first liquid medium, to effect the generation of chlorine dioxide from the chlorine dioxide precursor present in the first liquid medium. First and second outlets are also provided through which the first liquid medium and the second liquid medium, respectively, exit the first container section and the second container section, respectively. The first container section, second container section, first outlet and second outlets are components of a single article, for example, a single bottle.

In one particularly useful embodiment, the apparatus comprises a plurality of each of the first container sections, the second container sections, the first outlets and the second outlets. In this embodiment, the apparatus is preferably sized so that the combination of the first liquid medium from one of the first container sections and the second liquid medium from one of the second container sections is effective to produce sufficient chlorine dioxide to disinfect a pair of contact lenses present in the combination.

The present lens disinfecting preferably takes place in a single step. The lens wearer does not need to closely monitor the process or to change solutions. Preferably, no acidity adjusting is needed because the disinfecting occurs in the physiological pH range. Overall, the present invention is very easy and effective to use. This encourages the lens wearer to disinfect, and preferably clean, his/her contact lenses frequently, resulting in more comfort and less eye irritation.

DETAILED DESCRIPTION OF THE INVENTION

The present system is applicable for disinfecting all types of lenses, e.g., contact lenses, which are benefitted by periodical disinfecting. Such lenses, e.g., conventional hard contact lenses and soft contact lenses, may be made of any suitable material or combination of materials and may have any suitable configuration.

One important feature of the present invention is the use of chlorine dioxide precursors. Such precursors are adapted to provide for controlled formation of disinfecting amounts of chlorine dioxide. Thus, such precursors allow the disinfectant, chlorine dioxide, to be shipped and stored with minimum loss of disinfecting power. Chlorine dioxide is formed when needed and wanted, i.e., in a liquid medium contacting a lens to be disinfected. As used herein, a disinfecting amount of chlorine dioxide means such amount as will reduce the microbial burden or load by one log order in 3 hours or less, preferably in 1 hour or less, more preferably in 10 minutes or less. Of course, the amount of chlorine dioxide employed should not cause any substantial damage to the lens being treated.

In general, the chlorine dioxide precursors useful in the present invention are those which form or produce chlorine dioxide in a liquid medium, preferably a liquid aqueous medium, in the presence of one or more of the presently useful activator components. The liquid aqueous medium is preferably maintained at a pH in the range of about 6 to about 10, more preferably about 6 to about 8. Useful chlorine dioxide precursors include one or more chlorine dioxide-containing complexes and/or one or more chlorite-containing components and/or one or more other entities capable of forming chlorine dioxide in a liquid medium in the presence of the presently useful activator components.

Examples of such chlorite-containing components include metal chlorites, and in particular alkali metal and alkaline earth metal chlorites. A specific example of a chlorite-containing component which is useful as a chlorine dioxide precursor is technical grade sodium chlorite. Among the preferred chlorine dioxide-containing complexes are complexes of chlorine dioxide with carbonate, chlorine dioxide with bicarbonate and mixtures thereof. If the chlorine dioxide precursor is to be stored in a liquid medium before use, the preferred chlorine dioxide precursor useful in the present invention is stabilized chlorine dioxide. The exact chemical composition of stabilized chlorine dioxide is not completely understood. The manufacture or production of certain stabilized chlorine dioxide products is described in McNicholas U.S. Pat. No. 3,278,447, which is hereby incorporated in its entirety by reference herein. Specific examples of useful stabilized chlorine dioxide products include materials such as that sold under the trademark Dura Kior by Rio Linda Chemical Company, Inc. and that sold under the trademark Anthium Dioxide by International Dioxide, Inc. An especially useful stabilized chlorine dioxide product is a product sold under the trademark Purogene ® by Bio-Cide International, Inc.

The chlorine dioxide precursor may be included in a liquid medium at a predetermined concentration, e.g., a concentration chosen to provide a disinfecting amount of chlorine dioxide in the presence of the activator component or components. Preferably, the liquid medium has sufficient chlorine dioxide precursor so as to have a potential of producing chlorine dioxide in the range of about 0.002% to about 3% (weight chlorine dioxide/volume of liquid medium).

In one embodiment, the chlorine dioxide precursor includes a functionality selected from carbonate, borate, sulfate, phosphate, and mixtures thereof.

The presently useful activator components are selected from chlorine dioxide reducing components and mixtures thereof. Such activator components are capable of effecting the formation of a lens disinfecting amount, preferably a contact lens disinfecting amount, of chlorine dioxide from a chlorine dioxide precursor in a liquid medium into which the activator component is released. The activator component is preferably water soluble. In order to facilitate user convenience and to reduce the risk of eye irritation, the activator component is preferably ophthalmically acceptable. That is, the activator component in the concentrations used in the present invention is preferably such that it has substantially no significant long term detrimental effects on the ocular health of the wearer of a contact lens disinfected in accordance with the present invention.

Any suitable chlorine dioxide reducing component may be used in the present invention, provided that it functions as described herein and has no substantial detrimental effect on the lens being treated or on the human wearing the treated lens. Examples of useful chlorine dioxide reducing components include, but are not limited to, sulfur-containing components, such as SH (group)—containing water soluble lower alcohols, dithiothreitol, bisulfites, thio urea, betamercaptoethanol, 2-mercaptopropionic acid, 2-mercaptopropionylglycine, 2-mercaptoethylamine hydrochloride, dithioerythritol, sulfites, pyrosulfites, thiosulfates, dithionites, glutathione and the like; N-acetylcysteine; acetylcysteine; cysteine hydrochloride ethyl ester; homocysteine; carbamoylcysteine; cysteine; cysteine hydrochloride; cysteinyl glycine; and the like and mixtures thereof. A particularly useful chlorine dioxide reducing component is selected from thiosulfates, for example, alkali metal thiosulfates and hydrogen thiosulfate and mixtures thereof.

The amount of chlorine dioxide reducing component employed should be such as to be effective to effect formation of a lens, for example, a contact lens, disinfecting amount of chlorine dioxide in a chlorine dioxide precursor-containing liquid medium into which the chlorine dioxide reducing component is released. The chlorine dioxide reducing component is preferably present, for example, during the disinfecting contacting, in an amount less than that amount effective to reduce all the potential chlorine dioxide formable from the chlorine dioxide precursor in the liquid medium. The chlorine dioxide reducing component may be present in an amount in the range of about 0.01 mole or less to about 0.5 mole or more per mole of potential chlorine dioxide present as chlorine dioxide precursor in the liquid medium. Particularly useful results are achieved using amounts of chlorine dioxide reducing component in the range of about 0.01 mole to about 0.1 mole per mole of potential chlorine dioxide present as chlorine dioxide precursor in the liquid medium.

In one embodiment of the present invention, a solid composition is provided which includes a solid chlorine dioxide precursor in an amount more than that effective, when activated, to form a contact lens disinfecting amount of chlorine dioxide; and a solid activator component selected from chlorine dioxide reducing components and mixtures thereof. The solid activator component is present in an amount effective, for example, as noted above, when released into a liquid medium containing a soluble chlorine dioxide precursor derived from the solid chlorine dioxide precursor, to effect the formation of a contact lens disinfecting amount of chlorine dioxide from the soluble chlorine dioxide precursor. The activator component is preferably present in an amount less than that effective to reduce all the potential chlorine dioxide formable from the solid chlorine dioxide precursor. This composition is preferably in the form of a tablet, pill, granules or the like.

The liquid media useful in the present invention are selected to have no substantial detrimental effect on the lens being treated and to allow and even facilitate the present lens treatment or treatments. The liquid media are preferably aqueous-based. A particularly useful liquid aqueous medium is that derived from saline, for example, a conventional saline solution or a conventional buffered saline solution. During the disinfecting contacting, it is preferred that the liquid aqueous medium have a pH in the range of about 6 to about 10, more preferably about 6 to about 8, and still more preferably about 7.5. The liquid medium preferably has an ophthalmically acceptable tonicity level, for example, of at least about 200 mOsmol/kg, more preferably in the range of about 200 to about 400 mOsmol/kg.

After the disinfecting contacting, the disinfected lens can be contacted with e.g., rinsed and/or soaked in, a second liquid medium, e.g., a conventional saline or buffered saline solution, separate and apart from the liquid medium used in the disinfecting contacting. The second liquid medium preferably has a pH in the range of about 6 to about 10, more preferably about 6 to about 8, and still more preferably about 7.5. Such pH ranges are substantially consistent with the normal physiological pH for humans. Thus, a simple saline rinse or soak of the disinfected lens may be employed before placing the lens in the eye. Alternately, after disinfecting, the disinfected lens may be placed directly in the eye. It has been found that the small amounts of chlorine dioxide and chlorine dioxide precursor remaining in the liquid medium do not cause the liquid medium to be harmful or irritating to the eye. This is in contrast to other disinfection systems which require elaborate neutralization procedures before the lens is suitable for placement in the eye.

The disinfecting contacting preferably occurs at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. Contacting at or about ambient temperature is very convenient and useful. The contacting preferably occurs at or about atmospheric pressure. This contacting preferably occurs for a time to substantially completely disinfect the lens being treated. Such contacting times can be in the range of about 1 minute to about 12 hours or more.

In one embodiment, the present compositions include an enzyme component capable of removing debris from a contact lens. This component is present in an amount effective to remove debris from a contact lens located in a liquid medium into which the component is released. The composition is structured so that upon introduction into a liquid medium, the enzyme component is released before the activator component is released. The enzyme/lens contacting occurs in a liquid medium, preferably an aqueous liquid medium, such as described elsewhere herein. In a particularly useful embodiment, the enzyme/lens contacting occurs in the same container as does the lens disinfecting, more particularly in the same liquid medium as does the lens disinfecting. This "one-step" disinfecting/cleaning system is effective and very convenient for the lens wearer to use.

Among the types of debris that form on a contact lens during normal use are protein-based or proteinaceous debris, mucin-based debris, lipid-based debris and carbohydrate-based debris. One or more types of debris may be present on a single contact lens.

The enzyme or enzymes used are capable of removing at least one type of debris from a contact lens. The amount of such enzyme or enzymes used is preferably effective to remove substantially all of at least one type of debris from a debris laden contact lens in a reasonable time, preferably within about 12 hours, for example, in the range of about 1 minute to about 12 hours, and more preferably within about 2 hours, for example, about 1 minute to about 2 hours. The active enzyme-containing liquid medium preferably contains sufficient enzyme to provide between about 0.0001 to about 5 Anson units of activity, more preferably between about 0.001 or about 0.01 to about 0.1 or about 1 Anson unit, per single lens treatment. Higher or lower amounts may be used.

The enzyme employed may be selected from enzymes which are conventionally employed in the enzymatic cleaning of contact lenses. For example, many of the enzymes disclosed in Huth et al U.S. Pat. Re. No. 32,672 and Karageozian et al U.S. Pat. No. 3,910,296 are useful in the present invention. Each of these patents is incorporated in its entirety by reference herein. Among the useful enzymes are those selected from proteolytic enzymes, lipases and mixtures thereof. The enzyme may be one or more carbohydrate-active or carbolytic enzymes. Specific examples of useful enzymes include proteases, amylases, lipases and mixtures thereof.

Preferred proteolytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two sub-classes, subtilisin A and subtilisin B. In the subtilisin A grouping are enzymes derived from such species are *B. subtilis, B. licheniformis* and *B. pumilis*. Organisms in this sub-class produce little or no neutral protease or amylase. The subtilisin B sub-class is made up of enzymes from such organisms a *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example, overnight) of substantially all of at least one type of debris from a lens deposited due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective lens cleaner will depend on several factors, including the inherent activity of the enzyme.

Enzyme activity is pH dependent so for any given enzyme, there is a particular pH range in which that enzyme will function best. The determination of such range can readily be done by known techniques.

It has been found that many of the effective lens cleaning enzymes, such as described elsewhere herein, are inactivated in the presence of certain contact lens disinfectants. For example, a substantial number of such enzymes are inactive in the presence of disinfecting amounts of chlorine dioxide. Since the use of such enzyme incompatible (or simply incompatible) contact lens disinfectants is often advantageous in the contact lens disinfecting context, a system to allow both such disinfecting and enzymatic cleaning of contact lenses, preferably in one user initiated step, would clearly be advantageous. The present invention provides such a system.

In another embodiment, the activator component is included in the composition in a substantially inactive form and/or is released on a delayed release basis. For example, the enzyme and activator component can be present together in a single item, i.e., a layered tablet, pill or the like. After the item is introduced in the liquid medium containing the chlorine dioxide precursor, the enzyme first becomes available to remove debris from the to-be-cleaned lens. At this time, i.e., when the enzyme is cleaning the lens, the activator component remains in the item, effectively out of contact with the chlorine dioxide precursor. After a period of time, e.g., a predetermined period of time for which the item is designed, the activator component is released in the liquid medium. This causes chlorine dioxide formation which, in turn, results in disinfecting the lens in the liquid medium.

Tablets, pills, granules or the like which release their ingredients in a sequential, time delayed manner are well known and can be produced using conventional technology. Therefore, a detailed description of such items and such production technology is not presented here. However, such tablets, pills, granules or the like are preferably designed to allow one component sufficient time to perform its function before releasing another component which may interfere with the functioning of the first component. For example, if the item contains both an enzyme and an activator component, the item is preferably designed to allow the enzyme sufficient time to remove at least a major amount, and more preferably substantially all, of at least one type of debris, for example, protein-based debris, from the lens in the liquid medium. In other words, such items are preferably designed so that sufficient time elapses between release of the enzyme and release of the activator component to allow the enzyme to perform its cleaning function. Such sufficient time is preferably in the range of about one minute to about 2 hours, more preferably about five minutes to about one hour.

Although multi-layered (including core and coating layers) tablets or pills are preferred, the delayed release form of the present compositions can be present in any other suitable item or items, such as masses of powders, granules and the like. Delayed release technology is well known in the art as exemplified by the text *Controlled Drug Delivery*, 2nd Ed., Joseph R. Robinson & Vincent H. L. Lee, Eds., Marcel Dekker, Inc., New York, 1987.

Any suitable delayed release component or combination of delayed release components may be employed, provided that such component or components function as described herein and have no substantial detrimental effect on the other components present, on the lens being treated and on the human wearing the treated lens. The delayed release component is preferably at least partially, more preferably completely, water soluble. The delayed release component preferably comprises a major amount of at least one polymeric material. Examples of useful delayed release components include, but are not limited to, soluble cellulose ethers such as methylcellulose, methylhydroxypropylcellulose, methylhydroxyethylcellulose, hydroxypropylcellulose, hydroxyethylcellulose and sodium carboxymethylcelluloses; cellulose esters such as cellulose acetate phthalate and hydroxypropylmethylcellulose phthalate; polymers derived from at least one of acrylic acid, acrylic acid esters, methacrylic acid and methacrylic acid esters such as methacrylic acid-methyl methacrylate copolymer (for example that sold by Rohm Pharma under the trademark Eudragit L 100) and methacrylic acid-ethyl acrylate copolymers (for example that sold by Rohm Pharma under the trademark Eudragit L 30D); polymers derived from methyl vinyl ether and maleic acid anhydride; polyvinylpyrrolidone; polyvinyl alcohols and the like and mixtures thereof.

Figures 1, 2, 3, 4:
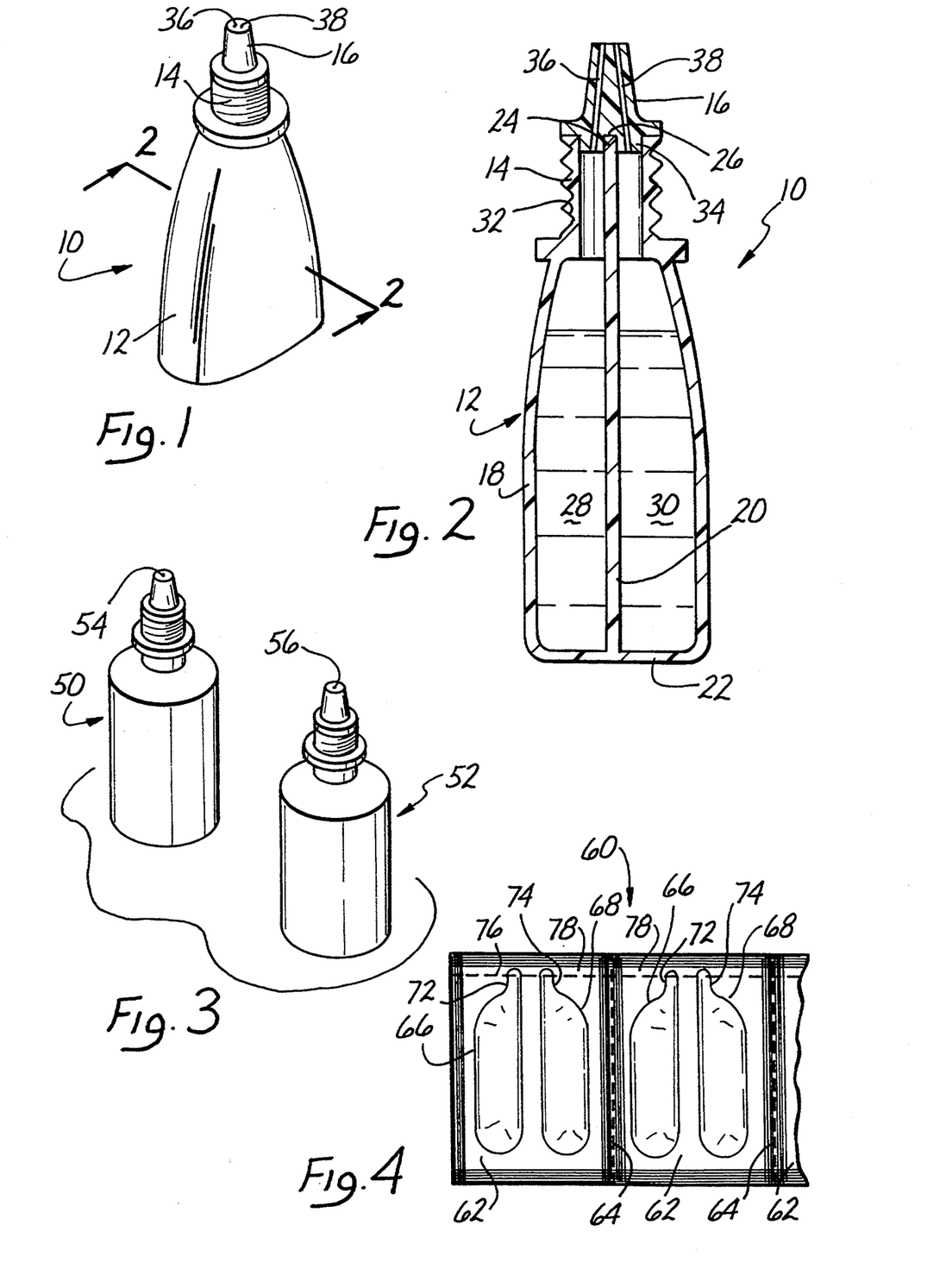
FIG. 1 is front side view, in perspective, of one embodiment of the apparatus in accordance with the present invention.
FIG. 2 is a cross-sectional view taken generally along line 2—2 of FIG. 1.
FIG. 3 is a front side view, in perspective, of a two bottle system useful in practicing the present invention.
FIG. 4 is a partial front plan view of another embodiment of the apparatus in accordance with the present invention.

Referring now to the drawings, FIGS. 1 and 2 illustrate a "single bottle" embodiment of the present apparatus. Specifically, this single bottle, shown generally as 10, includes a container body 12, a threaded upper portion 14, and an outlet tip portion 16.

The container body 12 includes an outer wall 18 and an inner partition 20 which extends upwardly from the bottom 22 of the container body. The upper end 24 of inner partition 20 is received in and held by notch 26 of outlet tip portion 16. Inner partition 20 divides the space defined by outer wall 18 and bottom 22 into a first container 28 and a second container 30, which are separate from each other.

The threaded upper portion 14 is hollow and includes an outer surface 32 which is adapted to engage a threaded bottle cap (not shown) to thereby secure the threaded bottle cap over the outlet tip portion 16 during periods of non-use of bottle 10.

The outlet tip portion 16 includes a lower portion 34 which is force fitted into the hollow space defined by threaded upper portion 14. The outlet tip portion 16 defines a first outlet conduit 36, which is in fluid communication with first container 28, and a second outlet conduit 38, which is in fluid communication with second container 30.

The various components making up bottle 12 can be made of any suitable polymeric material. Such material or materials should be such as to have no substantial detrimental effect on, and is not substantially detrimentally affected by, the liquid media present in the first and second containers 28 and 30, respectively. Examples of such suitable polymeric materials include polyethylene terephthalate, other polyethylene polyesters, low and high density polyethylenes, polypropylene and polyvinyl chloride.

The container body 12 should be constructed so as to be squeezable by the application of manual force to urge liquid from the first and second containers 28 and 30 out of the single bottle 10 through first and second outlet conduits 36 and 38, respectively. Bottle 10 is preferably constructed so that the application of a manual squeezing force between the two sides of container body 12 shown in FIG. 2 results in equal volumes of liquid medium exiting both first container 28 and second container 30.

First container 28 is filled with a buffered saline solution, having a pH of 7.5 and an osmolality of 300 mOsmol/kg, containing about 0.005% (w/v) of a stabilized chlorine dioxide product sold by Bio-Cide International, Inc. under the trademark Purogene ®. Second container 30, which is equal in volume to first container 28, is filled with a buffered saline solution, having a pH of 7.5 and an osmolality of 300 mOsmol/kg, containing about 0.005% (w/v) of sodium thiosulfate.

Bottle 10 is used as follows. When it is desired to disinfect a pair of contact lenses, they are placed in a conventional contact lens container. Bottle 10 is uncapped and turned upside down. Using manual force, container body 12 is squeezed, thereby urging equal quantities of first and second liquid media from bottle 10 into the lens container. After an appropriate amount (about 7.5-10 ml) of liquid has been passed to the lens container, the squeezing pressure is released and bottle 10 is uprighted. Thereafter, the bottle 10 is capped and stored. The liquid in the lens container is allowed to contact the contact lenses for about 4 hours. Thereafter, the lenses, which are now disinfected, can be removed from the lens container and placed directly in the eye for safe and comfortable wear. Alternately, the disinfected lenses can be rinsed in a conventional buffered saline solution before being placed in the eye.

FIG. 3 illustrates a "two bottle" system for practicing the present invention. A first bottle 50 and a second bottle 52 are filled with a first liquid medium and a second liquid medium, respectively. First and second bottles 50 and 52 are each made of a suitable polymeric material, as described above with regard to bottle 10. Each of the bottles 50 and 52 define only one container (no inner partition is included) and only a single outlet conduit 54 and 56, respectively, is included. The first liquid medium in first bottle 50 has a composition identical to the composition of the solution present in first container 28, while the second liquid medium in second bottle 52 has a composition identical to the composition of the solution in second container 30.

Bottles 50 and 52 are used as follows:

When it is desired to disinfect a pair of contact lenses, they are placed in a conventional contact lens container. Bottle 50 is uncapped and turned upside down. Using manual force, the bottle 50 is squeezed, thereby urging about 4–5 ml of the first liquid medium from bottle 50 into the lens container. After the first liquid medium is passed into the lens container, the squeezing pressure is released and bottle 50 is uprighted. In a similar manner, bottle 52 is uncapped and turned upside down. Using manual force, the bottle 52 is squeezed, thereby urging about 4–5 ml of the second liquid medium from bottle 52 into the lens container. After the second liquid medium is passed into the lens container, the squeezing pressure is released and the bottle 52 is uprighted. Thereafter, bottles 50 and 52 are capped and stored. The liquid in the lens container is allowed to contact the contact lenses for about 4 hours. Thereafter, the lenses, which are now disinfected, can be removed from the lens container and placed directly in the eye for safe and comfortable wear. Alternately, the disinfected lenses can be rinsed with a conventional buffered saline solution before being placed in the eye.

Referring now to FIG. 4, an alternate embodiment of the present apparatus is shown. In this embodiment, a strip of individual pairs of pouches, shown generally as 60, includes a series, for example, between 7 and about 10, individual strip sections 62. Each of these stripped sections 62 is a component of the strip 60 but can be separated from the other sections along perforations 64.

Each of the sections 62 include a first pouch 66 and a second pouch 68. Each of the first pouches 66 include about 4 to 5 ml of a first liquid medium having a composition identical to the solution as described included in first container 28. Each of the second pouches 68 include about 4 to about 5 ml of a second liquid medium having a composition identical to the solution in second container 30. Each of the first pouches 68 include a first outlet portion 72, while each of the second pouches 68 include a second outlet portion 74. The pouches are sealed along a top perforation 76.

The various components of strip 60 can be made of any suitable polymeric material. Such material or materials should be such as to have no substantial detrimental effect on, and is not substantially detrimentally affected by, the liquid media present in the first pouches 66 and second pouches 68. Examples of such suitable polymeric materials include polyethylene terephthalate, other polyethylene polyesters, low and high density polyethylenes, polypropylene and polyvinyl chloride.

Strip 60 is used as follows:

When it is desired to disinfect a pair of contact lenses, they are placed in a conventional contact lens container. One strip section 62 is separated along perforation 64 from the remainder of strip 60. The pouches are unsealed by ripping the top 78 from the remainder of the strip section 62 along perforation 76. Each of the pouches is then emptied into the lens container. The liquid in the lens container is allowed to contact the contact lenses for about 4 hours. Thereafter, the lenses, which are now disinfected, can be removed from the lens container and placed directly in the eye for safe and comfortable wear. Alternately, the disinfected lenses can be rinsed in a conventional buffered saline solution before being placed in the eye.

The following non-limiting examples illustrate certain aspects of the present invention.

EXAMPLES 1 TO 4

A series of four (4) activator tablets are prepared. These tablets have compositions as shown in Table 1.

TABLE 1

| Chlorine Dioxide Activator Tablet Formulations | | | | |
|---|---|---|---|---|
| Ingredients | Milligrams per tablet | | | |
| Sodium Thiosulfate | 1.5 | 0.5 | 0.25 | 0.05 |
| Polyvinyl-pyrollidone | 0.3 | — | — | — |
| Subtilisin A | 0.5 | — | — | — |
| Sugar-based binder/filler | 35.0 | 35.0 | 35.0 | 35.0 |
| Sodium carbonate, anhydrous | 18.0 | 18.0 | 18.0 | 18.0 |
| Tartaric acid | 7.0 | 7.0 | 7.0 | 7.0 |
| Polyethylene glycol 3350(1) | 6.0 | 6.0 | 6.0 | 6.0 |
| Tablet weight(mg) | 68.3 | 66.5 | 66.25 | 66.05 |
| Formula No. | I | II | III | IV |

(1) A conventional tabletting aid having a molecular weight of about 3350.

Each of these activator tablets is tested for chlorine dioxide generation using a standard solution. This solution was purified water with the following components: 0.85% (w/v) sodium chloride; 0.10% (w/v) boric acid; and 0.005% (w/v) a stabilized chlorine dioxide product sold by Bio-Cide International, Inc. under the trademark Purogene ®. The pH of this solution was buffered to about 7.7.

Each of the activator tablets is placed in 10 ml of the solution and the resulting material is monitored for chlorine dioxide concentration.

Each of the activator tablets tested effects the generation of sufficient chlorine dioxide to disinfect a contact lens within a reasonable period of time.

EXAMPLES 5 TO 8

An activator tablet having the composition of each of the activator tablets identified in Examples 1 to 4 is tested as follows. The activator tablet is placed in 10 ml of a solution of 0.005% (w/v) of the stabilized chlorine dioxide product noted in Examples 1 to 4 in purified water. After the tablet is dissolved, the pH and osmolality of the solution are determined.

Results of these indicate that the present activator tablets provide contact lens disinfecting media which have ophthalmically acceptable pHs and osmolalities. This is a substantial advantage of the present invention since no additional neutralization or acidity adjusting step is required. The disinfected lens can be removed from this solution and placed directly in the eye with little or no risk of eye irritation or discomfort.

EXAMPLE 9

A lens disinfecting system is provided which included a solution and an activator tablet The solution is purified water with the following components: 0.85% (w/v) sodium chloride; 0.10% (w/v) boric acid; and 0.005% (w/v) the stabilized chlorine dioxide product identified in Examples 1 to 4. The pH of this solution is about 7.7.

The activator tablet is as shown above as Formula No. II.

The activator tablet is placed in 10 ml of the solution along with a contact lens to be disinfected.

The amount of chlorine dioxide produced by combining the activator tablet with the solution is effective to kill most microorganisms in about 30 minutes or less.

The disinfected contact lens can be taken from the system and placed directly in the eye without irritation or discomfort.

EXAMPLE 10

Using conventional techniques, a layered delayed release tablet is prepared. The core of this tablet has the same chemical make-up as the activator tablet of Example 9. The outer layer of this tablet includes 0.71 mg of Subtilisin A. A delayed release barrier layer is located between the core and the outer layer and is designed to delay the release of the activator core in the solution for one hour after the layered tablet is introduced into the solution.

The solution which is used is as identified in Example 9.

The contact lens to be disinfected and the layered tablet are initially introduced into 10 ml of the solution at substantially the same time. The outer layer of the tablet dissolves into the solution very quickly, releasing the Subtilisin A enzyme into the solution to effectively clean the contact lens. After one hour, the activator core is released into the liquid medium and effects the generation of a contact lens disinfecting amount of chlorine dioxide. The cleaned and disinfected lens is then taken from the system, rinsed with a conventional saline solution to remove residual enzyme and placed in the eye for wear without irritation or discomfort.

EXAMPLE 11

Using conventional techniques, a layered delayed release tablet is prepared. The core of this tablet has the same chemical make-up as the activator tablet of Example 9. The outer layer of this tablet includes 0.71 mg of Subtilisin A and 1.1 mg of technical grade sodium chlorite. A delayed release barrier layer is located between the core and the outer layer and is designed to delay the release of the activator core in an aqueous medium for one hour after the layered tablet is introduced into the aqueous medium. The aqueous medium used is 10 ml of a conventional buffered saline solution.

The contact lens to be disinfected and the layered tablet are initially introduced into the liquid medium at substantially the same time. The outer layer of the tablet dissolves into the liquid medium very quickly, releasing the sodium chlorite and the Subtilisin A enzyme. This released Subtilisin A enzyme effectively cleans the contact lens. After one hour, the activator core is released into the liquid medium and effects the generation of a contact lens disinfecting amount of chlorine dioxide. The cleaned and disinfected lens is then taken from the system, rinsed with conventional saline solution to remove residual enzyme and placed into the eye for wear without irritation or discomfort.

While this invention has been described with respect to various specific examples and embodiments, it is to be understood that the invention is not limited thereto and that it can be variously practiced within the scope of the following claims.

What is claimed is:

1. A method for disinfecting a lens which comprises: contacting a lens to be disinfected with a liquid medium containing stabilized chlorine dioxide effective to form chlorine dioxide and an activator component selected from the group consisting of chlorine dioxide reducing components effective to chemically reduce chlorine dioxide in an amount effective to effect formation of a lens disinfecting amount of chlorine dioxide from said stabilized chlorine dioxide in said liquid medium, thereby disinfecting said lens to be disinfected.

2. The method of claim 1 wherein said liquid medium is an aqueous liquid medium and said contacting occurs at a pH in the range of about 6 to about 10, and said lens is a contact lens.

3. The method of claim 1 wherein said activator component is selected from the group consisting of sulfur-containing, chlorine dioxide reducing components.

4. The method of claim 1 wherein said activator component is selected from the group consisting of thiosulfates.

5. The method of claim 1 wherein said activator component is present in an amount less than that effective to reduce all the chlorine dioxide formable from said stabilized chlorine dioxide in said liquid medium.

6. The method of claim 1 which further comprises contacting the lens with an enzyme component in an amount and at conditions effective to remove debris from the lens.

7. The method of claim 6 wherein said enzyme component and said activator component are each part of a single item introduced into said liquid medium.

8. The method of claim 7 wherein said item includes a delayed release component effective to cause said item to release said enzyme component in said liquid medium prior to the release of said activator component in said liquid medium.

9. A composition useful for disinfecting a contact lens comprising:
a liquid medium containing stabilized chlorine dioxide effective to form chlorine dioxide in an amount more than that effective to form a contact lens disinfecting amount of chlorine dioxide; and
an activator component selected from the group consisting of chlorine dioxide reducing components effective to chemically reduce chlorine dioxide in an amount effective to effect formation of a contact lens disinfecting amount of chlorine dioxide from said stabilized chlorine dioxide in said liquid medium.

10. The composition of claim 9 wherein said liquid medium is an aqueous liquid medium and has a pH in the range of about 6 to about 10.

11. The composition of claim 9 wherein said activator component is selected from the group consisting of sulfur-containing, chlorine dioxide reducing components.

12. The composition of claim 9 wherein said activator component is selected from the group consisting of thiosulfates.

13. The composition of claim 9 wherein said activator component is present in an amount less than that effective to reduce all the chlorine dioxide formable from said stabilized chlorine dioxide in said liquid medium.

14. The composition of claim 9 which further comprises an enzyme component in an amount effective to removed debris from a contact lens.

15. The composition of claim 14 wherein said activator component and said enzyme component are each part of a single item, and said composition further comprises a delayed release component effective to cause said item to release said enzyme component in said liquid medium prior to the release of said activator component in said liquid medium.

16. A composition comprising a solid chlorine dioxide precursor in an amount more than that effective to form a contact lens disinfecting amount of chlorine dioxide; and a solid activator component selected from the group consisting of sulfur-containing chlorine dioxide reducing components effective to chemically release chlorine dioxide, said solid activator component being present in an amount effective, when released into a liquid medium containing a soluble chlorine dioxide precursor derived from said solid chlorine dioxide precursor, to effect the formation of a contact lens disinfecting amount of chlorine dioxide from said soluble chlorine dioxide precursor.

17. The composition of claim 16 wherein said solid activator component is present in an amount less than that effective to reduce all the chlorine dioxide formable from said solid chlorine dioxide precursor.

* * * * *